United States Patent
Althaus

(10) Patent No.: US 7,258,989 B2
(45) Date of Patent: Aug. 21, 2007

(54) CARBOHYDRATE DEFICIENT TRANSFERRIN (CDT) -SPECIFIC ANTIBODIES, THEIR PREPARATION AND USE

(75) Inventor: Harald Althaus, Wetter (DE)

(73) Assignee: Dade Behring Marburg GmbH, Marburg (DE)

( * ) Notice: Subject to any disclaimer, the term of this patent is extended or adjusted under 35 U.S.C. 154(b) by 243 days.

(21) Appl. No.: 10/612,162

(22) Filed: Jul. 3, 2003

(65) Prior Publication Data

US 2004/0014145 A1    Jan. 22, 2004

(30) Foreign Application Priority Data

Jul. 5, 2002  (DE) ............... 102 30 550
May 19, 2003  (EP) ............... 03011334

(51) Int. Cl.
*G01N 33/53* (2006.01)
*G01N 33/536* (2006.01)
*C12P 21/08* (2006.01)
*C07K 16/08* (2006.01)
*C07K 16/24* (2006.01)

(52) U.S. Cl. ............ 435/7.1; 435/7.92; 435/70.21; 435/810; 530/388.1; 530/388.15; 530/388.25

(58) Field of Classification Search ............ 530/388.24, 530/388.1, 388.15, 388.25; 435/810, 70.21, 435/7.1, 7.92

See application file for complete search history.

(56) References Cited

U.S. PATENT DOCUMENTS 5,702,904 A * 12/1997 Makhlouf et al. ........... 435/7.1

FOREIGN PATENT DOCUMENTS

| EP | 0 605 627 | 7/1994 |
| WO | 93/06133 | 4/1993 |
| WO | 99/00672 | 1/1999 |
| WO | 00/36418 | 6/2000 |

OTHER PUBLICATIONS

Kuby et al, Immunology, Second edition, pp. 86-96, 1994.*
Abaza et al, J of Protein Chemistry 11(5): 433-444, 1992.*
Duan et al., Generation of Carbohydrate-Deficient Transferrin by Enzymatic Deglycosylation of Human Transferrin, *Applied Biochemistry and Biotechnology*, 69:217-224 (1998).
Mason et al., "Expression of Glycosylated and Nonglycosylated Human Transferrin in Mammalian Cells. Characterization of the Recombinant Proteins with Comparison to Three Commerically Available Transferrins," *Biochemistry*, 32:5472-5479 (1993).
Messerschmid, "Erzeugung von polyklonalen Antikörpern in Nicht-Säugern," *BIOforum Forschung und Entwicklung*, 19:500-502 (1996) (English Abstract).
Wenschuh et al., "Coherent Membrane Supports for Parallel Microsynthesis and Screening of Bioactive Peptides," *Biopolymers*, 55:188-206 (2000).
Wilson et al., "Recent Developments in the Periodate Method of Conjugating Horseradish Peroxidase (HRPO) to Antibodies," In: *Immunofluorescence and Related Staining Techniques*, pp. 215-224 (1978).
Trimble et al., "Anti-Peptide Antibodies to Epitopes Masked by the Carbohydrate Moieties in Transferrin," *Biochemical Society Transactions*, 26:S48 (1998).
Althaus et al., "Development and Evaluation of a New Carbohydrate-Deficient Transferrin (CDT)-Specific Monoclonal Antibody," *Clinical Chemistry*, 49(6):A113 (2003).

* cited by examiner

Primary Examiner—Christina Chan
Assistant Examiner—Phuong Huynh
(74) Attorney, Agent, or Firm—Finnegan, Henderson, Farabow, Garrett and Dunner, L.L.P.

(57) ABSTRACT

The present invention relates to antibodies which, in agueous solution, selectively bind to a transferrin-homologous carbohydrate deficient transferrin (CDT) without the latter needing to be bound to a solid phase. CDT is characterized by at least one of the two oligosaccharide chains which are normally bound to Asn 413 and/or Asn 611 of transferrin being entirely or substantially entirely lacking.

11 Claims, No Drawings

CARBOHYDRATE DEFICIENT TRANSFERRIN (CDT) -SPECIFIC ANTIBODIES, THEIR PREPARATION AND USE

The present invention relates to antibodies which, in aqueous solution, selectively bind to a transferrin-homologous carbohydrate deficient transferrin (CDT) without the latter needing to be bound to a solid phase. CDT is characterized by at least one of the two oligosaccharide chains which are normally bound to Asn 413 and/or Asn 611 of transferrin being entirely or substantially entirely lacking.

Alcoholism is a problem around the world. A number of diagnostic tests for diagnosing alcoholism have been developed in the past. Most of these tests are, however, not specific for the disorder. The test which has been developed furthest to date was introduced by Makhlouf et al. in EP-0 605 627. The antibodies disclosed therein react specifically with CDT, which was found in alcoholics but not in non-alcoholics. This made it possible to design an immunoassay with whose aid it is possible to detect CDT in alcoholics' sera. However, the disadvantage of this test is that the antigen to be detected must firstly be coupled to a solid phase, because the antibodies disclosed in EP-0 605 627 do not bind, or bind only inadequately, to CDT which is present in solution.

The object therefore was to improve the CDT detection in such a way that direct detection of CDT present in solution in a sample becomes possible and thus there is no longer a need to couple the antigen to be detected to a solid phase.

This object has surprisingly been achieved by providing antibodies which bind selectively to CDT in aqueous solution without the latter needing to be bound to a solid phase. It has been found with the aid of epitope-mapping experiments that antibodies of the invention, in contrast to prior art antibodies, bind simultaneously to different segments of the CDT sequence. It was inferred from this that the epitopes recognized by the antibodies of the invention are discontinuous epitopes.

The present invention thus relates to an antibody which selectively binds to CDT in aqueous solution without the latter needing to be bound to a solid phase. It has been found that this antibody does not bind or binds insubstantially to the peptides P1 or P2 prepared according to EP-0 605 627, it being immaterial whether the peptides are bound to a solid phase or present in solution.

Selective binding means for the purposes of the present invention a sufficiently specific or substantially specific binding which makes it possible clearly to distinguish between CDT on the one hand and human transferrin on the other.

The term "solid phase" encompasses for the purposes of the present invention an article which consists of porous and/or nonporous, usually water-insoluble material and may have a wide variety of shapes, such as, for example, vessel, tube, microtiter plate, sphere, microparticle, rod, strip, filter paper or chromatography paper, etc. The surface of the solid phase is usually hydrophilic or can be made hydrophilic. The solid phase can consist of a wide variety of materials such as, for example, of inorganic and/or organic materials, of synthetic, of naturally occurring and/or of modified naturally occurring materials. Examples of solid phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon; ceramics; glass; metals, in particular noble metals such as gold or silver; magnetite; mixtures or combinations thereof; etc. It is also intended that the term "solid phase" include cells, liposomes or phospholipid vesicles.

The solid phase may have a coating of one or more layers, for example of proteins, carbohydrates, lipophilic substances, biopolymers, organic polymers or mixtures thereof, in order for example to diminish or to prevent nonspecific binding of constituents of samples to the solid phase or in order for example to achieve improvements in relation to the suspension stability of particulate solid phases, the storage stability, the dimensional stability or the resistance to UV light, microbes or other damaging agents.

The present invention additionally relates to an antibody which binds selectively to CDT, where the binding takes place in the region of the following segments (SEQ ID NOS: 1-4) of the CDT sequence:

| SEQ ID NO: 1 | VVARSMGGKEDLIWELL and |
| SEQ ID NO: 2 | TTEDSIAKIMNGEADAMSLDGGF and |
| SEQ ID NO: 3 | SKLSMGSGLNLSEPN and |
| SEQ ID NO: 4 | YEKYLGEEYVKAV. |

The present invention further relates to an antibody of this type whose binding takes place only in the region of only three or of only two of the aforementioned segments (1) to (4) of the sequence.

In a preferred embodiment, the antibodies of the invention are monoclonal antibodies.

Very particularly preferred monoclonal antibodies are those produced by cell cultures which were deposited under the Budapest Treaty at the DSMZ Deutsche Sammlung von Mikroorganismen und Zellkulturen GmbH, Mascheroder Weg 1b, 38124 Brunswick, Germany on Apr. 16, 2002 (accession date at the depository) as follows:
Cell culture 01-102/01 accession number: DSM ACC2541
Cell culture 98-84/011 accession number: DSM ACC2540

Antigen-binding fragments, for example Fab, Fab', Fv or F(ab')$_2$ fragments, which can be prepared from the aforementioned antibodies of the invention by processes known to every skilled worker, are also according to the invention.

The term "antibody" generally means for the purposes of this invention not only complete antibodies but expressly also antibody fragments such as the Fab, Fv, F(ab')$_2$ or Fab' fragments already mentioned, and also chimeric, humanized, bi- or oligospecific, or single-chain antibodies; additionally aggregates, polymers and conjugates of immunoglobulins and/or fragments thereof, as long as the binding properties to the antigen or hapten are retained. Antibody fragments can be prepared for example by enzymatic cleavage of antibodies with enzymes such as pepsin or papain. Antibody aggregates, polymers and conjugates can be generated by diverse methods, e.g. by thermal treatment, reaction with substances such as glutaraldehyde, reaction with immunoglobulin-binding molecules, biotinylation of antibodies and subsequent reaction with streptavidin or avidin, etc.

An antibody can be for the purposes of this invention a monoclonal or a polyclonal antibody. The antibody can have been prepared by conventional processes, e.g. by immunization of a human or of an animal such as for example, mouse, rat, guinea-pig, rabbit, horse, sheep, goat, chicken (see also Messerschmid (1996) BIOforum, 11:500-502), and subsequent obtaining of the antiserum; or by establishment of hybridoma cells and subsequent purification of the secreted antibodies; or by cloning and expression of the nucleotide sequences, or modified versions thereof, which encode the amino acid sequences which are responsible for the binding of the natural antibody to the antigen and/or hapten.

The present invention additionally relates to a process for preparing an antibody of the invention by immunizing a suitable experimental animal with unglycosylated transferrin or CDT, subsequently fusing the spleen cells of this experimental animal to myeloma cells, resulting in antibody-producing hybrid cells, and subsequently cloning the hybrid cells and selecting a hybrid cell clone which produces an antibody which selectively binds to CDT in aqueous solution without the latter needing to be bound to a solid phase. Finally, antibodies are obtained by a process known to the skilled worker from the hybrid cell clone selected in this way.

The present invention further relates to a process for preparing an antibody by immunizing a suitable experimental animal with unglycosylated transferrin or CDT, subsequently fusing the spleen cells of this experimental animal to myeloma cells, resulting in antibody-producing hybrid cells, and subsequently cloning the hybrid cells and selecting a hybrid cell clone which produces an antibody whose binding according to the results of an epitope mapping takes place in the region of the following segments (SEQ ID NOS:1-4) of a CDT sequence:

```
SEQ ID NO: 1    VVARSMGGKEDLIWELL and
SEQ ID NO: 2    TTEDSIAKIMNGEADAMSLDGGF and
SEQ ID NO: 3    SKLSMGSGLNLSEPN and
SEQ ID NO: 4    YEKYLGEEYVKAV;
``` followed finally by obtaining antibodies by a process known to the skilled worker from the hybrid cell clone selected in this way.

In place of unglycosylated transferrin or CDT, it is possible to use for the immunization of a suitable experimental animal in accordance with one of the aforementioned processes also a peptide comprising one or more of segments (1) to (4) of the sequence. The skilled worker is additionally aware that a short peptide which consists for example only of a single one or more than one of the aforementioned segments of the sequence can where appropriate be bound to a suitable carrier molecule to achieve adequate immunogenicity. Carrier molecules suitable for this purposes for example peptides or proteins, are known to the skilled worker.

The preparation processes described above encompass the hybridoma technology which is known to every skilled worker for the preparation of monoclonal antibodies, as was published for the first time in 1975 by Köhler and Milstein and has since been modified or improved by numerous authors. Although this technology has frequently been used for preparing monoclonal antibodies from mouse cells, there are also publications which describe the preparation of monoclonal antibodies of another origin. In addition, processes for preparing antibody constructs have also been disclosed, for example humanized or bi- or oligospecific or chimeric antibodies, which can of course likewise be employed for preparing antibodies of the invention.

The present invention also relates to an immunoassay for detecting CDT in a sample; this entails an antibody of the invention described above or a corresponding antibody fragment being brought into contact with the sample and then the formation of an immune complex involving CDT being determined qualitatively or quantitatively.

Test kits for carrying out an aforementioned immunoassay, comprising an antibody of the invention or an antibody fragment of the invention are likewise an aspect of the present invention.

The present invention is additionally explained by the following examples. These serve exclusively to illustrate by way of example individual aspects of the present invention and are by no means to be understood as a restriction.

EXAMPLES

Example 1

Preparation of Anti-human Transferrin-Sepharose

For the affinity purification of transferrin from human sera (normal sera and alcoholics' sera), an affinity support was prepared by coupling 120 mg of anti-human transferrin (Dade Behring Marburg GmbH, Marburg, Germany) to 0.8 g of CNBr-activated Sepharose CL-4B. 120 mg of anti-human transferrin are dialyzed against 0.1M $NaHCO_3$ solution. 0.8 g of Sepharose CL-4B (Amersham Biosciences Europe GmbH, Freiburg, Germany) is washed with 0.1M $NaHCO_3$ solution and, while cooling, 1.28 g of cyanogen bromide dissolved in 5 ml of acetonitrile are added. The suspension is stirred at pH 11 and 4° C. for 15 minutes. The suspension is then thoroughly washed with 0.1M $NaHCO_3$ solution. The activated Sepharose is suspended in 0.1M $NaHCO_3$ solution, and the prepared antibody solution is added and incubated at room temperature for 6 hours. The anti-human transferrin-Sepharose prepared in this way is washed with phosphate-buffered saline of pH 7.2 and stored in phosphate-buffered saline of pH 7.2+1 g/l $NaN_3$ until used.

Example 2

Isolation of Human Transferrin from Human Serum (Normal Serum and Alcoholic's Serum)

For the affinity purification of transferrin from human serum, the anti-human transferrin-Sepharose prepared in example 1 is packed into a glass column and washed with 100 ml of phosphate-buffered saline of pH 7.2+1g/l $NaN_3$. 10 ml of human serum (normal serum and alcoholic's serum) are loaded onto the column at a flow rate of 0.5 ml/minute, and the unbound proteins are removed by washing the column with 50 ml of phosphate-buffered saline of pH 7.2+1 g/l $NaN_3$, 50 ml of 1M NaCl solution and 50 ml of water. The bound transferrin is eluted with 50 ml of 0.5M glycine solution whose pH has been adjusted to pH 2.5 with hydrochloric acid, immediately neutralized by adding solid tris(hydroxymethyl)aminomethane and dialyzed against phosphate-buffered saline of pH 7.2+1 g/l $NaN_3$.

Example 3

Unglycosylated Human Transferrin a) Recombinant Unglycosylated Human Transferrin Recombinant unglycosylated transferrin is prepared with the aid of conventional methods of genetic manipulation and molecular biology and is described in Mason et al. (1993) Biochemistry, 32: 5472-5479.

b) Enzymatic Deglycosylation of Human Transferrin 60 mg of human transferrin (e.g. from Calbiochem-Novabiochem GmbH, Bad Soden, Germany) are dissolved in 8 ml of phosphate-buffered saline of pH 7.2 with 10 mM EDTA and 1 g/l (w/v) sodium decyl sulfate (from Fluka, order No.: 71443). The transferrin solution prepared in this way is heated to 37° C. in a water bath, and 180 units (3 units/mg transferrin) of N glycosidase F (from Roche, order No. 1365193) are added. The mixture is incubated in a water bath at 37° C. for 17 hours. The completeness of deglycosylation is investigated by SDS-PAGE (Duan et al. (1998) Applied Biochemistry and Biotechnology, 69: 217-224).

Example 4

Preparation of Monoclonal Antibodies According to the Prior Art

The preparation of monoclonal antibodies according to the prior art took place as described in the patent EP-0 605 627 B1 by immunization with transferrin-specific peptide sequences P1 and P2. The following hybrids/monoclonal antibodies were obtained:

| Antibody number: | Specificity: |
|---|---|
| 01-32/062 | anti-P1 |
| 00-177/012 | anti-P1 |
| 00-137/016 | anti-P2 |
| 00-187/027 | anti-P2 |

Example 5

Preparation of the Monoclonal Antibodies of the Invention a) Immunization of Mice BALB/c mice were each immunized intraperitoneally with 20 µg of unglycosylated transferrin in complete Freund's adjuvant. A booster was given after 4 weeks with in each case 20 µg of unglycosylated transferrin in incomplete Freund's adjuvant (from ICN Biomedical GmbH, Eschwege, Germany) and after 8 weeks with in each case 20 µg of unglycosylated transferrin without Freund's adjuvant. For the last 3 days before the fusion, the mice were given intravenous boosters each of 20 µg of unglycosyated transferrin.

b) Fusion

After the mice had been sacrificed by $CO_2$ inhalation, the spleens were removed and single-cell suspensions in serum-free Dulbecco's modified Eagle Medium (DMEM, from CC Pro GmbH, Neustadt/W, Germany) were prepared. The cells were centrifuged (652 g) and washed 2× in DMEM. The cell count was then determined by Trypan Blue staining. $2 \times 10^7$ myeloma cells (Sp2/0) were added to about $10^8$ spleen cells. After centrifugation (360 g), the supernatant was discarded, 1 ml of polyethylene glycol solution (PEG 400, from Merck Eurolab, Bruchsal, Germany; about 50% strength in DMEM) was added to the cell pellet and incubated after resuspension at 37° C. for 1 minute. About 10 ml of DMEM were then added dropwise, and the mixture was incubated at room temperature for 2 to 4 minutes. The fused cells were spun down (326 g) and the pellet was resuspended in DMEM+20% FCS (fetal calf serum, from Biowhittaker Europe, Verviers, Belgium)+HAT solution (from CC Pro GmbH, Neudstadt/W, Germany) and introduced into 24-well cell culture plates (from Costar). The approximate cell concentration per well was $5 \times 10^4$ to $5 \times 10^6$ cells.

2-3 weeks later, the resulting cell colonies (hybrids) were removed and transferred into new culture plates.

c) Determination of the Antibody Specificity

The specificity of the antibodies released into the cell culture was tested in a first test step using immunizing antigen-coated microtiter plates (from Nunc, type B), coating 1 µg/ml≈0.015 µg/well.

100 µl of cell culture supernatant (dilution 1:2) were pipetted into each well of the microtiter plate and incubated at +15 to +25° C. for 1 hour. After the plate had been washed twice with washing solution POD (OSEW; from Dade Behring, Marburg, Germany), 100 µl of anti-mouse IgG/F (ab')$_2$-POD conjugate (from Dade Behring, Marburg, Germany) were introduced into each well and then incubated at +15 to +25° C. for 1 hour. After the plate had been washed a further two times, 100 µl of chromogen TMB solution (from Dade Behring, Marburg, Germany) were introduced into each well and incubated at +15 to +25° C. for a further 30 minutes. After the incubation, 100 µl of stop solution POD (from Dade Behring, Marburg, Germany) were introduced into each well, and the microtiter plate was evaluated in a BEP II (Behring ELISA processor II, from Dade Behring, Marburg, Germany) at 450 nm.

In a second test step, the hybrids were checked as described above using microtiter plates (from Nunc, type B), which were coated with human transferrin (for example from Calbiochem-Novabiochem GmbH, Bad Soden, Germany). Coating 1 µg/ml≈0.015 µg/well.

The results are listed in table 1.

TABLE 1

Determination of the antibody specificity by evaluation of the microtiter plates in a BEP II (Behring ELISA processor II) at 450 nm

| | Extinction at 450 nm | |
|---|---|---|
| Hybrid number | Unglycosylated human transferrin | Human transferrin |
| 98-22/026 (569) | >2.5 | negative |
| 98-23/07 (45) | >2.5 | negative |
| 98-22/0104 (572) | 1.739 | negative |
| 98-84/011 (1) | >2.5 | negative |
| 01-102/01 (113) | >2.5 | negative |

Key:
negative = extinction$_{(450\ nm)}$ < 0.1 OD; no gradation of the signal on dilution of the hybrids investigated d) Cloning Single cells of hybrids which produce the antibodies of the invention (binding to unglycosylated human transferrin but not to human transferrin) were cloned using a micromanipulator (from Leitz, Wetzlar, Germany). The clones 98-84/011 and 01-102/01 obtained in this way were deposited on Apr. 16, 2002 at the DSMZ Deutsche Sammlung Mikroorganismen und Zellkulturen GmbH, Mascheroder Weg 1b, Brunswick, Germany, under accession number DSM ACC2540 (98-84/011) and DSM ACC2541 (01-102/01).

e) Determination of the Antibody Subclass

The subclass of the antibodies 98-84/011 and 01-102/01 was determined using IsoStrip™ mouse monoclonal antibody isotyping kit from Boehringer Mannheim, Germany, to be IgG$_1$ for 98-84/011 and 01-102/01.

f) Antibody Production

To produce larger quantities of antibodies, the appropriate cell clones are transferred into roller bottles (from Corning Costar Deutschland, Bodenheim) and expanded at +37° C. to the desired final volume. A 0.22 μm filtration of the roller culture suspension is then carried out to remove the cells. The antibody solution, which is now cell-free, is concentrated in an ultrafilter (separation limit 30 000 dalton) and then purified.

g) Antibody Purification

The resulting antibody solution is rebuffered to 0.14M phosphate buffer of pH 8.6, and loaded onto a chromatography column packed with rProtein A Sepharose Fast Flow (from Amersham Pharmacia) (1 ml of rprotein A Sepharose Fast Flow is employed per 10 mg of antibodies to be purified). All unbound components are removed by washing the column with 0.14M phosphate buffer of pH 8.6. The bound antibody is eluted from the column with 0.1M citric acid of pH 3.0 and dialyzed against 0.05M sodium acetate+ 0.5M NaCl+0.05M Tris+0.01% sodium azide of pH 7.0.

Example 6

Determination of the Specificity of the Antibodies for Solid Phase-bound Antigens: Comparison of Antibodies of the Invention with Prior art Antibodies The specificity of the antibodies obtained was tested using a) microtiter plates (Nunc, type B) coated with unglycosylated transferrin, coating 1 μg/ml≈0.015 μg/well, b) microtiter plates (Nunc type B) coated with human transferrin, coating 1 μg/ml≈0.015 μg/well, c) microtiter plates (Nunc, type B) coated with peptide P1 coating 3 μg/ml≈0.045 μg/well and d) microtiter plates (Nunc type B) coated with peptide P2, coating 3 μg/ml≈0.045 μg/well.

100 μl of monoclonal antibodies (1 μg/ml) were pipetted into each well of the microtiter plate and incubated at +15 to +25° C. for 1 hour. After the plate had been washed twice with washing solution POD (OSEW; from Dade Behring, Marburg, Germany), 100 μl of anti-mouse IgG/F(ab')$_2$-POD conjugate (from Dade Behring, Marburg, Germany) were introduced into each well and then incubated at +15 to +25° C. for 1 hour. After the plate had been washed a further two times, 100 μl of chromogen TMB solution (from Dade Behring, Marburg, Germany) were introduced into each well and incubated at +15 to +25° C. for a further 30 minutes. After the incubation, 100μl of stop solution POD (from Dade Behring, Marburg, Germany) were introduced into each well, and the microtiter plate was evaluated in a BEP II (from Dade Behring, Marburg, Germany) at 450 nm.

The results are listed in table 2.

TABLE 2

Determination of the antibody specificity by evaluation of microtiter plates in BEP II at 450 nm.

| | Extinction at 450 nm | | | |
|---|---|---|---|---|
| Antibody | Unglycosylated human transferrin | Human transferrin | Peptide P1 | Peptide P2 |
| Antibodies of the invention | | | | |
| 98-22/026 | 1.578 | negative | negative | negative |
| 98-23/07 | 2.497 | negative | negative | negative |
| 98-22/0104 | 1.179 | negative | negative | negative |
| 98-84/011 | >2.5 | negative | negative | negative |
| 01-102/01 | 2.432 | negative | negative | negative |
| Prior art anti-peptide P1 antibodies | | | | |
| 00-177/012 | 1.063 | 0.157 | >2.5 | negative |
| 01-32/062 | >2.5 | 0.151 | >2.5 | negative |
| Prior art anti-peptide P2 antibodies | | | | |
| 00-187/016 | 2.339 | negative | negative | >2.5 |
| 00-187/027 | >2.5 | negative | negative | >2.5 |

Key:
negative extinction$_{450\ nm}$ < 0.1 OD; no gradation of the signal on dilution of the hybrids investigated The antibodies of the invention show only a reaction with unglycosylated transferring while the prior art antibodies show a reaction with each peptide and with the unglycosylated transferrin bound to the solid phase.

Example 7

Determination of the Specificity of the Antibodies for Antigens in Solution: Comparison of Antibodies of the Invention with Prior Art Antibodies a) Microtiter plates (Nunc, type B) were coated with the monoclonal antibodies of the invention and with prior art monoclonal antibodies. Coating concentration 1 μg/ml≈0.015 μg/well.

100 μl of a geometric dilution series starting at 200 μg/ml of a) human transferrin, b) enzymatically deglycosylated human transferrin, c) human transferrin from normal serum and d) human transferrin from alcoholic's serum were pipetted into the wells of the microtiter plate and incubated at +15 to +25° C. for 1 hour. After the plate had been washed twice with washing solution POD (OSEW; from Dade Behring, Marburg, Germany), 100 μl of anti-human transferrin-POD conjugate (from Dade Behring, Marburg, Germany) were introduced into each well and then incubated at +15 to +25° C. for 1 hour. After the plate had been washed a further two times, 100 μl of chromogen TMB solution (from Dade Behring, Marburg, Germany) were introduced into each well and incubated at +15 to +25° C. for a further 30 minutes. After the incubation, 100 μl of stop solution POD (from Dade Behring, Marburg, Germany) were introduced into each well, and the microtiter plate was evaluated in a BEP II (from Dade Behring, Marburg, Germany) at 450 nm.

The results are listed in table 3.1 and 3.2.

TABLE 3.1

Determination of the reactivity by evaluation of microtiter plates in a BEP II at 450 nm.

Extinction at 450 min

| Antigen | Conc. [µg/ml] | Antibodies of the invention | | | Prior art antibodies | | | Antigen | Conc. [µg/ml] | Antibodies of the invention | | | Prior art antibodies | | |
| | | 98-23/07 | 98-84/011 | 01-102/01 | 01-32/062 | 00-187/016 | 00-187/027 | | | 98-23/07 | 98-84/011 | 01-102/01 | 01-32/062 | 00-187/016 | 00-187/027 |
|---|---|---|---|---|---|---|---|---|---|---|---|---|---|---|---|
| Human transferrin | 200 | 1.790 | 2.5 | 0.137 | negative | 0.508 | 0.553 | Unglycosylated human transferrin | 200 | 2.500 | 2.500 | 1.773 | 0.388 | 2.500 | 2.500 |
| | 100 | 0.664 | 2.5 | negative | negative | 0.230 | 0.291 | | 100 | 2.500 | 2.500 | 1.582 | 0.262 | 2.193 | 2.500 |
| | 50 | 0.541 | 2.5 | negative | negative | 0.123 | 0.170 | | 50 | 2.500 | 2.500 | 1.570 | 0.160 | 1.406 | 2.133 |
| | 25 | 0.491 | 2.5 | negative | negative | negative | negative | | 25 | 2.500 | 2.500 | 1.601 | 0.104 | 0.714 | 1.134 |
| | 12.5 | 0.320 | 2.5 | negative | negative | negative | negative | | 12.5 | 2.500 | 2.500 | 1.274 | negative | 0.442 | 0.588 |
| | 6.25 | 0.158 | 2.5 | negative | negative | negative | negative | | 6.25 | 2.500 | 2.500 | 1.238 | negative | 0.233 | 0.320 |
| | 3.125 | negative | 1.880 | negative | negative | negative | negative | | 3.125 | 2.500 | 2.500 | 1.230 | negative | 0.133 | 0.183 |
| | 1.56 | negative | 0.604 | negative | negative | negative | negative | | 1.56 | 2.500 | 2.500 | 0.880 | negative | negative | negative |
| | 0.781 | negative | 0.407 | negative | negative | negative | negative | | 0.781 | 2.500 | 2.500 | 0.890 | negative | negative | negative |
| | 0.391 | negative | 0.284 | negative | negative | negative | negative | | 0.391 | 2.500 | 2.500 | 0.722 | negative | negative | negative |
| | 0.195 | negative | 0.169 | negative | negative | negative | negative | | 0.195 | 2.500 | 2.500 | 0.436 | negative | negative | negative | negative: extinction$_{(450\ nm)}$ < 0.1 OD
positive: extinction$_{(450\ nm)}$ ≧ 0.1 OD

TABLE 3.2

Determination of the reactivity by evaluation of microtiter plates in a BEP II at 450 nm.

Extinction at 450 nm

| Antigen | Conc. [µg/ml] | Antibodies of the invention | | | Prior art antibodies | | | Antigen | Conc. [µg/ml] | Antibodies of the invention | | | Prior art antibodies | | |
| | | 98-23/07 | 98-84/011 | 01-102/01 | 01-32/062 | 00-187/016 | 00-187/027 | | | 98-23/07 | 98-84/011 | 01-102/01 | 01-32/062 | 00-187/016 | 00-187/027 |
|---|---|---|---|---|---|---|---|---|---|---|---|---|---|---|---|
| Human transferrin from normal serum | 200 | 1.309 | 2.5 | 0.188 | negative | 0.142 | 0.192 | Human transferrin from alcoholic's serum | 200 | 0.508 | 2.5 | negative | negative | 0.118 | 0.133 |
| | 100 | 0.229 | 2.5 | 0.116 | negative | negative | 0.158 | | 100 | 0.660 | 2.5 | negative | negative | negative | negative |
| | 50 | 0.177 | 2.5 | negative | negative | negative | 0.111 | | 50 | 0.306 | 2.5 | negative | negative | negative | negative |
| | 25 | 0.141 | 2.5 | negative | negative | negative | negative | | 25 | 0.252 | 2.5 | negative | negative | negative | negative |
| | 12.5 | 0.100 | 2.5 | negative | negative | negative | negative | | 12.5 | 0.181 | 2.5 | negative | negative | negative | negative |
| | 6.25 | negative | 2.5 | negative | negative | negative | negative | | 6.25 | 0.101 | 2.5 | negative | negative | negative | negative |
| | 3.125 | negative | 2.5 | negative | negative | negative | negative | | 3.125 | negative | 2.5 | negative | negative | negative | negative |
| | 1.56 | negative | 1.234 | negative | negative | negative | negative | | 1.56 | negative | 2.5 | negative | negative | negative | negative |
| | 0.781 | negative | 0.745 | negative | negative | negative | negative | | 0.781 | negative | 2.5 | negative | negative | negative | negative |
| | 0.391 | negative | 0.450 | negative | negative | negative | negative | | 0.391 | negative | 1.676 | negative | negative | negative | negative |
| | 0.195 | negative | 0.245 | negative | negative | negative | negative | | 0.195 | negative | 0.920 | negative | negative | negative | negative | negative: extinction$_{450\ nm}$ < 0.1 OD
positive: extinction$_{(450\ nm)}$ ≧ 0.1 OD b) Microtiter plates (Nunc, type B) were coated with the monoclonal antibodies of the invention and with prior art monoclonal antibodies. Coating concentration 3 µg/m≈0.045 µg/well.

100 µl of a geometric dilution series starting at a 1:10 dilution of a) normal serum and b) alcoholic's serum were pipetted into the wells of the microtiter plate and incubated at +15 to +25° C. for 1 hour. After the plate had been washed twice with washing solution POD (OSEW; from Dade Behring, Marburg, Germany), 100 µl of anti-human transferrin-POD conjugate (from Dade Behring, Marburg, Germany) were introduced into each well and then incubated at +15 to +25° C. for 1 hour. After the plate had been washed a further two times, 100 µl of chromogen TMB solution (from Dade Behring, Marburg, Germany) were introduced into each well and incubated at +15 to +25° C. for a further 30 minutes. After the incubation, 100 µl of stop solution POD (from Dade Behring, Marburg, Germany) were introduced into each well, and the microtiter plate was evaluated in a BEP II (from Dade Behring, Marburg, Germany) at 450 nm.

The results are listed in table 4.

TABLE 4

Determination of the reactivity by evaluation of microtiter plates in a BEP II at 450 nm.

| | | Extinction at 450 nm | | | | | | | | | | | | |
|---|---|---|---|---|---|---|---|---|---|---|---|---|---|---|
| | | Antibodies of the invention | | | | Prior art antibodies | | | Antibodies of the invention | | | | Prior art antibodies | |
| Antigen | Dilution | 98-23/07 | 98-22/0104 | 98-84/011 | 01-102/01 | 01-32/062 | 00-187/016 | Antigen | Dilution | 98-23/07 | 98-22/0104 | 98-84/011 | 01/102/01 | 01-32/062 | 00-187/016 |
| Normal human serum | 1:10 | 0.318 | 0.512 | 2.5 | 0.150 | negative | negative | Alcoholic human serum | 1:10 | 0.603 | 0.861 | 2.5 | 0.220 | negative | negative |
| | 1:20 | 0.212 | 0.313 | 2.5 | negative | negative | negative | | 1:20 | 0.367 | 0.545 | 2.5 | 0.148 | negative | negative |
| | 1:40 | 0.146 | 0.193 | 2.5 | negative | negative | negative | | 1:40 | 0.259 | 0.391 | 2.5 | 0.103 | negative | negative |
| | 1:80 | 0.107 | 0.104 | 2.5 | negative | negative | negative | | 1:80 | 0.165 | 0.205 | 2.5 | negative | negative | negative |
| | 1:160 | negative | negative | 2.5 | negative | negative | negative | | 1:160 | 0.128 | 0.155 | 2.5 | negative | negative | negative |
| | 1:320 | negative | negative | 1.605 | negative | negative | negative | | 1:320 | 0.110 | 0.118 | 2.5 | negative | negative | negative |
| | 1:640 | negative | negative | 0.936 | negative | negative | negative | | 1:640 | negative | negative | 2.5 | negative | negative | negative | negative: extinction$_{(450\ nm)}$ < 0.1 OD
positive: extinction$_{(450\ nm)}$ ≧ 0.1 OD The antibodies of the invention make it possible to differentiate clearly between transferrin (in normal serum) and CDT (in alcoholic's serum), while the prior art antibodies show no reaction with both sera.

Example 8

Epitope Mapping

Scans of overlapping peptides derived from the sequence of human transferrin (13-mer peptides, 11 amino acids overlapping) were prepared using the SPOT synthesis technology. The methods are described in: Wenschuh, H. et al. (2000) Coherent membrane supports for parallel microsynthesis and screening of bioactive peptides, *Biopolymers (Peptide Science)*, 55:188-206. The peptides were coupled at the C terminus to a cellulose support and carry a reactivity tag at the N terminus. After the peptides had been cleaved off cut-out SPOTs (96-well microtiter plate), they were coupled to activated glass chips. The incubation protocol for these glass chips is as follows:

Prior Art Monoclonal Antibodies
equilibration in TBS buffer, pH 8.0
blocking buffer, pH 8.0, 2 h
antibody incubation (3 µg/ml in blocking buffer, pH 8.0), 2 h
washing with TBS (0.05% Tween20)
incubation with anti-mouse IgG-POD in blocking buffer, pH 8.0, 2 h
washing with TBS (0.05% Tween20) 3×5 min
chemoluminescence detection (Lumi-Imager, Roche Diagnostics)

Antibody 98-84/011 of the Invention
equilibration in TBS buffer, pH 8.0
blocking buffer, pH 8.0, 2 h
antibody incubation (3 µg/ml) in blocking buffer, pH 8.0, 2 h
washing with TBS (0.05% Tween20) 3×5 min
chemoluminescence detection (Lumi-Imager, Roche Diagnostics)

The antibody of the invention was directly labeled with peroxidase. The method is described in the literature: Wilson, M. B. and Nakane, P. K. (1978) Recent developments in the periodate method of conjugating horseradish peroxidase (HRPO) to antibodies, In: Immunofluorescence and Related Staining Techniques (Eds.: Knapp, W.; Holubar, K.; Wick, G.) pp. 215-224.

After evaluation of the investigation, the binding peptides for the prior art antibodies are the following dominant segments of SEQ ID NO: 5 and SEQ ID NO:6:

```
Prior art antibodies against peptide 1
(SEQ ID NO: 5)
        1.      VLAENYNKSDNCE

2.      AENYNKSDNCEDT

3.      NYNKSDNCEDTPE

4.      NKSDNCEDTPEAG

Prior art antibodies against peptide 2
(SEQ ID NO: 6)
        1.      VHKILRQQQHLFG

2.      KILRQQQHLFGSN

3.      LRQQQHLFGSNVT

4.      QQQHLFGSNVTDC

5.      QHLFGSNVTDCSG
```

The recognized sequences are identical to the peptides employed for the immunization.

The antibody 98-84/011 of the invention reacts with a dominant segment of each of SEQ ID NOS: 1-4.

```
SEQ ID NO: 1
        1.      VVARSMGGKEDLI

2.      ARSMGGKEDLIWE

3.      SMGGKEDLIWELL

SEQ ID NO: 2
        4.      TTEDSIAKIMNGE

5.      SIAKIMNGEADAM

6.      AKIMNGEADAMSL

7.      IMNGEADAMSLDG

8.      NGEADAMSLDGGF
```

-continued

SEQ ID NO: 3
9.  SKLSMGSGLNLSE
10. LSMGSGLNLSEPN

SEQ ID NO: 4
11. YEKYLGEEYVKAV

Region 1.-3. is located in the N-terminal domain of transferrin, while regions 4.-8., 9.-10. and 11. are located in the C-terminal domain and represent a discontinuous epitope.

SEQ ID NO: 1    VVARSMGGKEDLIWELL and
SEQ ID NO: 2    TTEDSIAKIMNGEADAMSLDGGF and
SEQ ID NO: 3    SKLSMGSGLNLSEPN and
SEQ ID NO: 4    YEKYLGEEYVKAV.

2. An isolated antibody which binds selectively to carbohydrate deficient transferrin, wherein the binding takes place

What is claimed is:

1. An isolated antibody or an antigen binding fragment thereof which binds selectively to carbohydrate deficient transferrin, wherein the binding takes place in the region of the following four epitopes (1) to (4) of the carbohydrate deficient transferrin sequence:

in the region of three of the following four epitopes (1) to (4) of the carbohydrate deficient transferrin sequence:

SEQ ID NO: 1    VVARSMGGKEDLIWELL and
SEQ ID NO: 2    TTEDSIAKIMNGEADAMSLDGGF and -continued

```
SEQ ID NO: 3    SKLSMGSGLNLSEPN and
SEQ ID NO: 4    YEKYLGEEYVKAV;
```

3. An isolated antibody which binds selectively to carbohydrate deficient transferrin, wherein the binding takes place in the region of two of the following four epitopes (1) to (4) of the carbohydrate deficient transferrin sequence:

```
SEQ ID NO:1    VVARSMGGKEDLIWELL         and
SEQ ID NO:2    TTEDSIAKIMNGEADAMSLDGGF   and
SEQ ID NO:3    SKLSMGSGLNLSEPN           and
SEQ ID NO:4    YEKYLGEEYVKAV.
```

4. The antibody as claimed in claim 1, which is a monoclonal antibody.

5. A monoclonal antibody which is produced by the cell culture having the deposit number DSM ACC2540.

6. A monoclonal antibody which is produced by the cell culture having the deposit DSM ACC2541.

7. A process for preparing the antibody as claimed in claim 1 by immunizing a suitable experimental animal with unglycosylated transferrin, fusing the spleen cells of this experimental animal to myeloma cells, resulting in antibody-producing hybrid cells, cloning the hybrid cells and selecting a hybrid cell clone which produces an antibody whose binding according to the results of an epitope mapping takes place in the region of the following four epitopes (1) to (4) of the carbohydrate deficient transferrin sequence:

```
SEQ ID NO:1    VVARSMGGKEDLIWELL         and
SEQ ID NO:2    TTEDSIAKIMNGEADAMSLDGGF   and
SEQ ID NO:3    SKLSMGSGLNLSEPN           and
SEQ ID NO:4    YEKYLGEEYVKAV;
``` and obtaining antibody from the selected hybrid cell clone.

8. An immunoassay for detecting carbohydrate deficient transferrin in a sample, which comprises contacting the antibody as claimed in claim 1 with the sample, and detecting the formation of an immune complex consisting of carbohydrate deficient transferrin and said antibody.

9. A test kit for carrying out an immunoassay as claimed in claim 8 comprising the antibody which binds selectively to carbohydrate deficient transferrin, wherein the antibody binding takes place in the region of at least two of the following four epitopes (1) to (4) of the carbohydrate deficient transferrin sequence:

```
SEQ ID NO:1    VVARSMGGKEDLIWELL         and
SEQ ID NO:2    TTEDSIAKIMNGEADAMSLDGGF   and
SEQ ID NO:3    SKLSMGSGLNLSEPN           and
SEQ ID NO:4    YEKYLGEEYVKAV.
```

10. The test kit as claimed in claim 9, wherein the antibody binding takes place in the region of three of the following four epitopes (1) to (4) of the carbohydrate transferrin sequence:

```
SEQ ID NO:1    VVARSMGGKEDLIWELL         and
SEQ ID NO:2    TTEDSIAKIMNGEADAMSLDGGF   and
SEQ ID NO:3    SKLSMGSGLNLSEPN           and
SEQ ID NO:4    YEKYLGEEYVKAV.
```

11. The test kit as claimed in claim 9, wherein the antibody binding takes place in the region of all four of the following epitopes (1) to (4) of the carbohydrate transferrin sequence:

```
SEQ ID NO:1    VVARSMGGKEDLIWELL         and
SEQ ID NO:2    TTEDSIAKIMNGEADAMSLDGGF   and
SEQ ID NO:3    SKLSMGSGLNLSEPN           and
SEQ ID NO:4    YEKYLGEEYVKAV.
```

* * * * *

SEQUENCE LISTING

```
<160> NUMBER OF SEQ ID NOS: 4

<210> SEQ ID NO 1
<211> LENGTH: 17
<212> TYPE: PRT
<213> ORGANISM: Homo sapiens

<400> SEQUENCE: 1

Val Val Ala Arg Ser Met Gly Gly Lys Glu Asp Leu Ile Trp Glu Leu
 1               5                  10                  15

Leu

<210> SEQ ID NO 2
<211> LENGTH: 23
<212> TYPE: PRT
<213> ORGANISM: Homo sapiens

<400> SEQUENCE: 2

Thr Thr Glu Asp Ser Ile Ala Lys Ile Met Asn Gly Glu Ala Asp Ala
 1               5                  10                  15

Met Ser Leu Asp Gly Gly Phe
            20

<210> SEQ ID NO 3
<211> LENGTH: 15
<212> TYPE: PRT
<213> ORGANISM: Homo sapiens

<400> SEQUENCE: 3

Ser Lys Leu Ser Met Gly Ser Gly Leu Asn Leu Ser Glu Pro Asn
 1               5                  10                  15

<210> SEQ ID NO 4
<211> LENGTH: 13
<212> TYPE: PRT
<213> ORGANISM: Homo sapiens

<400> SEQUENCE: 4

Tyr Glu Lys Tyr Leu Gly Glu Glu Tyr Val Lys Ala Val
 1               5                  10
```